(12) United States Patent
Mitts et al.

(10) Patent No.: US 7,410,481 B1
(45) Date of Patent: Aug. 12, 2008

(54) URETHRAL CATHETER DEVICE AND METHOD OF USING

(76) Inventors: Cheryl A. Mitts, 3277 Hedingham Ct., Las Vegas, NV (US) 89135; Lawrence E. Klecka, 3277 Hedingham Ct., Las Vegas, NV (US) 89135

( * ) Notice: Subject to any disclaimer, the term of this patent is extended or adjusted under 35 U.S.C. 154(b) by 765 days.

(21) Appl. No.: 10/819,068

(22) Filed: Apr. 6, 2004

(51) Int. Cl.
*A61M 27/00* (2006.01)

(52) U.S. Cl. ..................... 604/544; 604/317

(58) Field of Classification Search ............ 604/540, 604/264, 265, 275, 276, 103.02, 523, 544, 604/533, 349–350, 321, 317, 96.01, 244, 604/246–247
See application file for complete search history.

(56) References Cited

U.S. PATENT DOCUMENTS

| | | | |
|---|---|---|---|
| 3,529,599 A * | 9/1970 | Folkman et al. ............. 604/323 |
| 4,280,498 A * | 7/1981 | Jensen ..................... 604/335 |
| 4,349,029 A | 9/1982 | Mott |
| 4,553,959 A | 11/1985 | Hickey et al. |
| 4,623,329 A * | 11/1986 | Drobish et al. ............... 604/29 |
| 4,704,102 A * | 11/1987 | Guthery ..................... 604/28 |
| 4,932,938 A | 6/1990 | Goldberg et al. .......... 604/99.04 |
| D315,411 S | 3/1991 | Reif et al. |
| 5,112,306 A | 5/1992 | Burton et al. |
| 5,306,226 A * | 4/1994 | Salama ...................... 600/29 |
| 5,417,657 A | 5/1995 | Hauer |
| 5,429,620 A * | 7/1995 | Davis ........................ 604/538 |
| 5,971,950 A * | 10/1999 | Lopez et al. ................. 604/500 |
| 6,283,940 B1 | 9/2001 | Mulholland |
| 7,150,740 B2 * | 12/2006 | Bennett et al. ............... 604/544 |
| 2005/0124978 A1 * | 6/2005 | Kim ........................... 604/544 |
| 2007/0066965 A1 * | 3/2007 | Coambs et al. .............. 604/533 |

* cited by examiner

*Primary Examiner*—Nicholas D. Lucchesi
*Assistant Examiner*—Theodore J Stigell

(57) ABSTRACT

A urethral catheter device and an associated method of using the device are disclosed. The device comprises a catheter probe and at least one receiving unit attachable to the probe for receiving and collecting urine. The catheter probe comprises: an elongated shaft, a valve, a drainage lumen, a drainage inlet, a tapered cone, a collar, an elongated protuberance, a saline inlet, a saline lumen, a sheath, and a fluid lock. Each receiving unit comprises: a sterile membrane, a sleeve, and a collection bag. When the sleeve of the receiving unit is attached to the collar of the catheter probe, then the tapered cone of the catheter probe ruptures the membrane of the receiving unit, whereby the drainage inlet of the proximate end of the catheter probe is fluidly connected to the collection bag of the catheter probe and the valve is thereby opened. The sheath attached at the proximate end of the elongated shaft is inflatable into a donut shaped balloon which is capable of being retained within a bladder of a patient. The method of using the device comprises the steps of aligning, forcing, holding, injecting, inserting, lubricating, positioning, releasing, removing, sliding, slipping, turning, and twisting.

20 Claims, 3 Drawing Sheets

URETHRAL CATHETER DEVICE AND METHOD OF USING

FIELD OF THE INVENTION

The present invention relates to medical devices, more particularly to a urethral catheter device and a method of using the device for draining urine from a bladder of a patient.

DESCRIPTION OF THE PRIOR ART

Urinary Drainage catheters, such as the Foley catheter, are hollow, tubular devices commonly used in the medical profession for insertion into a patient's bladder via the urethral tract to permit the drainage of urine. Use of urinary catheters is necessary for patients that are undergoing surgery, orthopedically incapacitated, incontinent, or incapable of voluntary urination. A wide variety of catheters is currently available on the commercial market and an even larger number of these types of devices are known in the art of catheters, for example, the drainage balloon catheter system disclosed by Mott in U.S. Pat. No. 4,349,029; the urethral catheter disclosed by Hickey and Brocklehurst in U.S. Pat. No. 4,553,959; the method and apparatus for valving body fluids disclosed by Burton et al. in U.S. Pat. No. 5,112,306; the no-sepsis urinary drainage catheter disclosed by Hauer in U.S. Pat. No. 5,417,657; the catheter disclosed by Mulholland in U.S. Pat. No. 6,283,940; and the urinary catheter disclosed by Reif et al. in U.S. Pat. No. D315,411.

While all of the above-described devices fulfill their respective, particular objectives and requirements, the aforementioned patents do not describe a urethral catheter device having a catheter probe with at least one receiving unit attachable to the probe for receiving and collecting urine, wherein the catheter probe includes an elongated shaft with a valve, a drainage lumen, a drainage inlet, a tapered cone, a collar, an elongated protuberance, a saline inlet, a saline lumen, a sheath, and a fluid lock and wherein each receiving unit comprises: a sterile membrane, a sleeve, and a collection bag. This combination of elements would specifically match the user's particular individual needs of making it possible to use the device in the steps of aligning, forcing, holding, injecting, inserting, lubricating, positioning, releasing, removing, sliding, slipping, turning, and twisting. The above-described patents make no provision for a catheter probe with at least one receiving unit attachable to the probe for receiving and collecting urine, wherein the catheter probe includes an elongated shaft, a drainage lumen, a drainage inlet, a tapered cone, a collar, an elongated protuberance, a saline inlet, a saline lumen, a sheath, and a fluid lock and wherein each receiving unit comprises: a sterile membrane, a sleeve, and a collection bag.

Therefore, a need exists for a new and improved urethral catheter device having a catheter probe with at least one receiving unit attachable to the probe for receiving and collecting urine, wherein the catheter probe includes an elongated shaft, a drainage lumen, a drainage inlet, a tapered cone, a collar, an elongated protuberance, a saline inlet, a saline lumen, a sheath, and a fluid lock and wherein each receiving unit comprises: a sterile membrane, a sleeve, and a collection bag. In this respect, the urethral catheter device according to the present invention substantially departs from the conventional concepts and designs of the prior art, and in doing so provides an apparatus primarily developed for the purpose of providing a means for aligning, forcing, holding, injecting, inserting, lubricating, positioning, releasing, removing, sliding, slipping, turning, and twisting.

SUMMARY OF THE INVENTION

The present device and method of using, according to the principles of the present invention, overcomes the shortcomings of the prior art by providing a urethral catheter device and method of using are disclosed. The device comprises a catheter probe and at least one receiving unit attachable to the probe for receiving and collecting urine. The catheter probe comprises: an elongated shaft with a valve on the distal end, a drainage lumen, a drainage inlet, a tapered cone, a collar, an elongated protuberance, a saline inlet, a saline lumen, a sheath, and a fluid lock. Each receiving unit comprises: a sterile membrane, a sleeve, and a collection bag. When the sleeve of the receiving unit is attached to the collar of the catheter probe, then the tapered cone of the catheter probe ruptures the membrane of the receiving unit which opens the valve, whereby the drainage inlet of the proximate end of the catheter probe is fluidly connected to the collection bag of the catheter probe. The sheath attached at the proximate end of the elongated shaft is inflatable into a donut shaped balloon which is capable of being retained within a bladder of a patient. The method of using the device comprises the steps of aligning, forcing, holding, injecting, inserting, lubricating, positioning, releasing, removing, sliding, slipping, turning, and twisting.

In view of the foregoing disadvantages inherent in the known type catheter devices now present in the prior art, the present invention provides an improved urethral catheter device, which will be described subsequently in great detail, is to provide a new and improved urethral catheter device which is not anticipated, rendered obvious, suggested, or even implied by the prior art, either alone or in any combination thereof.

To attain this, the present invention essentially comprises an elongated shaft with a valve in the distal end, a drainage lumen, a drainage inlet, a tapered cone, a collar, an elongated protuberance, a saline inlet, a saline lumen, a sheath, and a fluid lock. Each receiving unit comprises: a sterile membrane, a sleeve, and a collection bag. When the sleeve of the receiving unit is attached to the collar of the catheter probe, then the tapered cone of the catheter probe ruptures the membrane of the receiving unit and opens the valve, whereby the drainage inlet of the proximate end of the catheter probe is fluidly connected to the collection bag of the catheter probe. The sheath attached at the proximate end of the elongated shaft is inflatable into a donut shaped balloon which is capable of being retained within a bladder of a patient.

There has thus been outlined, rather broadly, the more important features of the invention in order that the detailed description thereof that follows may be better understood, and in order that the present contribution of the art may be better appreciated.

The invention may also include cap attached to the rim of the sleeve of the receiving unit. There are of course, additional features of the invention that will be described hereinafter and which will form the subject matter of the claims attached.

Numerous objects, features and advantages of the present invention will be readily apparent to those of ordinary skill in the art upon reading of the following detailed description of presently preferred, but nonetheless illustrative, embodiments of the present invention when taken in conjunction with the accompany drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved urethral catheter device that has all the advantages of the prior art urethral catheter device and none of the disadvantages.

It is another object of the present invention to provide a new and improved urethral catheter device that may be easily and efficiently manufactured and marketed.

An even further object of the present invention is to provide a new and improved urethral catheter device that has a low cost of manufacture with regard to both materials and labor, and which accordingly is then susceptible of low prices of sale to the consuming public, thereby making such multipurpose storage unit and system economically available to the buying public.

Still another object of the present invention is to provide a new urethral catheter device that provides in the apparatuses and methods of the prior art some of the advantages thereof, while simultaneously overcoming some of the disadvantages normally associated therewith.

Even still another object of the present invention is to provide a urethral catheter device having a catheter probe with at least one receiving unit attachable to the probe for receiving and collecting urine, wherein the catheter probe includes an elongated shaft with a valve in the distal end, a drainage lumen, a drainage inlet, a tapered cone, a collar, an elongated protuberance, a saline inlet, a saline lumen, a sheath, and a fluid lock and wherein each receiving unit comprises: a sterile membrane, a sleeve, and a collection bag. This combination of elements makes it possible to use the device in the steps of aligning, forcing, holding, injecting, inserting, lubricating, positioning, releasing, removing, sliding, slipping, turning, and twisting.

Lastly, it is an object of the present invention to provide a new and improved method of using comprising the steps of aligning, forcing, holding, injecting, inserting, lubricating, positioning, releasing, removing sliding, slipping, turning, and twisting.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and description matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DETAILED DESCRIPTION OF THE PREFERRED EMBODIMENT

Figure 1:
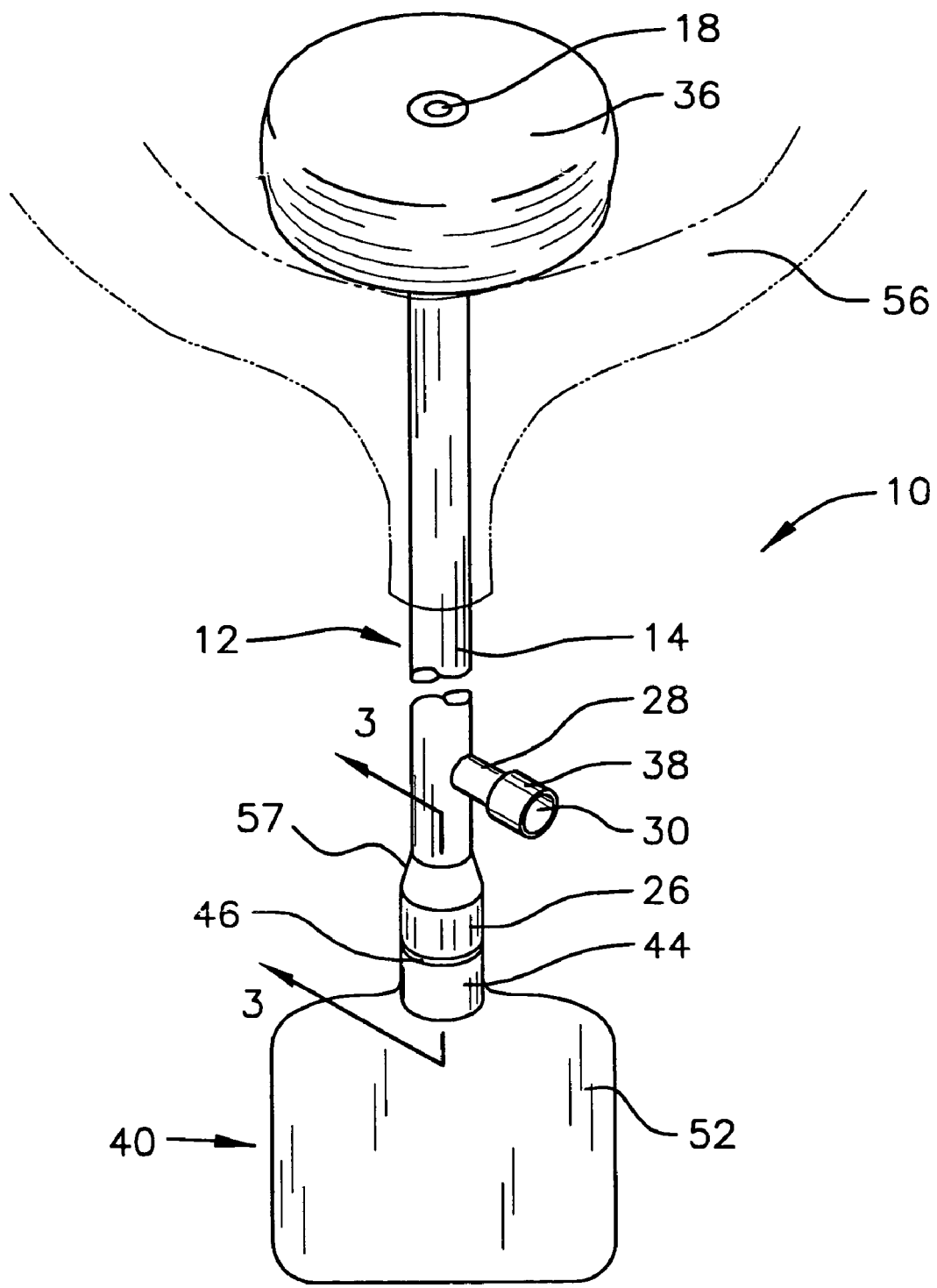
FIG. 1 is a perspective view of a preferred embodiment of the urethral catheter device constructed in accordance with the principles of the present invention.

Referring now to the drawings, and in particular FIGS. 1 to 5 thereof, one preferred embodiment of the present invention is shown and generally designated by the reference numeral 10. One preferred embodiment of a urethral catheter device 10 comprises: a catheter probe 12 and at least one receiving unit 40 attachable to the probe 12. The catheter probe 12 comprises: an elongated shaft 14, a drainage lumen 16, a drainage inlet 18, a tapered cone 20, a collar 26, an elongated protuberance 28, a saline inlet 30, a saline lumen 32, a sheath 36, and a fluid lock 38. The elongated shaft 14 includes: an interior side wall; an exterior side wall; a middle section; a proximate end for insertion into a bladder 56 of a patient; a distal end for pending outside the bladder 56 of the patient; and an internal wall disposed between the interior side wall and the exterior side wall, wherein the internal wall of the shaft 14 defining a lip disposed at the exterior side wall of the shaft 14, the lip defining a saline outlet 34 disposed in the proximate end of the shaft 14. The drainage lumen 16 is defined by the interior side wall of the shaft 14, in which the drainage lumen 16 provides fluid communication between the proximate end of the shaft 14 and the distal end of the shaft 14. The drainage inlet 18 comprises a drainage opening defined by the drainage lumen 16 at the proximate end of the shaft 14, wherein the drainage inlet 18 is for receiving urine from the bladder 56. The tapered cone 20 is attached to the proximate end of the shaft 14, in which the cone 20 has a pointed head 24 and a drainage outlet 22, wherein the drainage outlet 22 of the cone 20 is in fluid communication with the drainage inlet 18, whereby the drainage outlet 22 is for discharging urine. The collar 26 is attached to the distal end of the shaft 14, wherein the collar 26 has an annular interior wall, in which the interior wall of the collar 26 has two ridges defining an annular channel disposed around the interior wall of the collar 26. The elongated protuberance 28 is attached to the middle section of the shaft 14, wherein the protuberance 28 includes: a distal end, the distal end of the protuberance 28 is attached to the middle section of the shaft 14; a proximate end; an inner side wall, the inner side wall of the protuberance 28 connected to the internal wall of the shaft 14; and an outer side wall. The saline inlet 30 is defined by the inner side wall of the protuberance 28, in which the saline inlet 30 is disposed at the proximate end of the protuberance 28, whereby the saline inlet 30 for receiving saline. The saline lumen 32 is defined by the internal wall of the shaft 14 and the inner side wall of the protuberance 28, wherein the saline lumen 32 is in fluid communications with the saline inlet 30 of the protuberance 28 and the saline outlet 34 of the shaft 14. The sheath 36 is circumferentially attached around the proximate end of the shaft 14, in which the sheath 36 defines a void space between the sheath 36 and the proximate end of the shaft 14. The void space is in fluid communications with saline outlet 34 disposed of the shaft 14. When the void space is empty then the sheath 36 is collapsed around the proximate end of the shaft 14. When the void space is filled with saline then the sheath 36 expands into a donut shaped balloon, the drainage inlet 18 disposed outside of the balloon. The fluid lock 38 is pivotally attached to the proximate end of the protuberance 28, wherein the fluid lock 38 is in fluid communications with the saline inlet 30. When the fluid lock 38 is turned in a given direction then the fluid lock 38 is placed in an open position so that the saline inlet 30 is in fluid communications with the surrounding environment of the device 10. When the fluid lock 38 is rotated in an opposite direction relative to the given direction then the fluid lock 38 is in a closed position wherein the saline inlet 30 is not in fluid communications with the surrounding environment of the device 10. Each receiving unit 40 of the at least one receiving unit 40 comprises: a sterile membrane 42, a sleeve 44, and a collection bag 52. The sleeve 44 is attached to the membrane 42. The sleeve 44 has a rim 46, an annular outside wall, and an annular inside wall. The rim 46 of the sleeve 44 is attached to the membrane 42. The annular outside wall has an annular ring 48 attached around the outside wall, in which the annular outside wall is proportioned to slidably insert within the collar 26 of the distal end of the shaft 14, wherein the ring 48 of the outside wall of the sleeve 44 is shaped to slidably lock within the annular channel disposed around the interior wall of the collar 26 of the distal end of the shaft 14. When the sleeve 44 is inserted within the collar 26 of the distal end of the shaft 14 then the membrane 42 is punctured with the pointed head 24 of the cone 20 of the shaft 14. The annular inside wall defines a urine collection inlet 50. The collection bag 52 is attached to the sleeve 44, in which the collection bag 52 in fluid communications with the urine collection inlet 50 of the sleeve 44.

An optional cap 54 may be added to the device 10. Each cap 54 is attached to the outside wall of the sleeve 44 of each corresponding receiving unit 40 of the at least one receiving unit 40, wherein the sterile membrane 42 of each receiving unit 40 of the at least one receiving unit 40 is disposed between the cap 54 and the rim 46 of the sleeve 44.

Another preferred embodiment of the urethral catheter device 10 consists essentially of: a catheter probe 12, at least one receiving unit 40 attachable to the probe 12 and at least one cap 54 attached to each receiving unit 40. The catheter probe 12 comprises: an elongated shaft 14, a drainage lumen 16, a drainage inlet 18, a tapered cone 20, a collar 26, an elongated protuberance 28, a saline inlet 30, a saline lumen 32, a sheath 36, and a fluid lock 38. The elongated shaft 14 includes: an interior side wall; an exterior side wall; a middle section; a proximate end for insertion into a bladder 56 of a patient; a distal end forpending outside the bladder 56 of the patient; and an internal wall disposed between the interior side wall and the exterior side wall, wherein the internal wall of the shaft 14 defining a lip disposed at the exterior side wall of the shaft 14, the lip defining a saline outlet 34 disposed in the proximate end of the shaft 14. The drainage lumen 16 is defined by the interior side wall of the shaft 14, in which the drainage lumen 16 provides fluid communication between the proximate end of the shaft 14 and the distal end of the shaft 14. The drainage inlet 18 comprises a drainage opening defined by the drainage lumen 16 at the proximate end of the shaft 14, wherein the drainage inlet 18 is for receiving urine from the bladder 56. The tapered cone 20 is attached to the proximate end of the shaft 14, in which the cone 20 has a pointed head 24 and a drainage outlet 22, wherein the drainage outlet 22 of the cone 20 is in fluid communication with the drainage inlet 18, whereby the drainage outlet 22 is for discharging urine. The collar 26 is attached to the distal end of the shaft 14, wherein the collar 26 has an annular interior wall, in which the interior wall of the collar 26 has two ridges defining an annular channel disposed around the interior wall of the collar 26. The elongated protuberance 28 is attached to the middle section of the shaft 14, wherein the protuberance 28 includes: a distal end, the distal end of the protuberance 28 is attached to the middle section of the shaft 14; a proximate end; an inner side wall, the inner side wall of the protuberance 28 connected to the internal wall of the shaft 14; and an outer side wall. The saline inlet 30 is defined by the inner side wall of the protuberance 28, in which the saline inlet 30 is disposed at the proximate end of the protuberance 28, whereby the saline inlet 30 for receiving saline. The saline lumen 32 is defined by the internal wall of the shaft 14 and the inner side wall of the protuberance 28, wherein the saline lumen 32 is in fluid communications with the saline inlet 30 of the protuberance 28 and the saline outlet 34 of the shaft 14. The sheath 36 is circumferentially attached around the proximate end of the shaft 14, in which the sheath 36 defines a void space between the sheath 36 and the proximate end of the shaft 14. The void space is in fluid communications with saline outlet 34 disposed of the shaft 14. When the void space is empty then the sheath 36 is collapsed around the proximate end of the shaft 14. When the void space is filled with saline then the sheath 36 expands into a donut shaped balloon, the drainage inlet 18 disposed outside of the balloon. The fluid lock 38 is pivotally attached to the proximate end of the protuberance 28, wherein the fluid lock 38 is in fluid communications with the saline inlet 30. When the fluid lock 38 is turned in a given direction then the fluid lock 38 is placed in an open position so that the saline inlet 30 is in fluid communications with the surrounding environment of the device 10. When the fluid lock 38 is rotated in an opposite direction relative to the given direction then the fluid lock 38 is in a closed position wherein the saline inlet 30 is not in fluid communications with the surrounding environment of the device 10. Each receiving unit 40 of the at least one receiving unit 40 comprises: a sterile membrane 42, a sleeve 44, and a collection bag 52. The sleeve 44 is attached to the membrane 42. The sleeve 44 has a rim 46, an annular outside wall, and an annular inside wall. The rim 46 of the sleeve 44 is attached to the membrane 42. The annular outside wall has an annular ring 48 attached around the outside wall, in which the annular outside wall is proportioned to slidably insert within the collar 26 of the distal end of the shaft 14, wherein the ring 48 of the outside wall of the sleeve 44 is shaped to slidably lock within the annular channel disposed around the interior wall of the collar 26 of the distal end of the shaft 14. When the sleeve 44 is inserted within the collar 26 of the distal end of the shaft 14 then the membrane 42 is punctured with the pointed head 24 of the cone 20 of the shaft 14. The annular inside wall defines a urine collection inlet 50. The collection bag 52 is attached to the sleeve 44, in which the collection bag 52 in fluid communications with the urine collection inlet 50 of the sleeve 44. Each cap 54 of the at least one cap 54 is attached to the outside wall of the sleeve 44 of each receiving unit 40 of the at least one receiving unit 40, wherein the sterile membrane 42 of each receiving unit 40 of the at least one receiving unit 40 is disposed between the cap 54 and the rim 46 of the sleeve 44.

The capacity of the balloon created by expanding the sheath 36 attached to the proximate end of the shaft 14 may have any volumetric displacement. One preferred configuration is that the void space between the sheath 36 and the proximate end of the shaft 14 has a volumetric capacity of at least five milliliters of saline. Another preferred configuration of the void space between the sheath 36 and the proximate end of the shaft 14 has a volumetric capacity of up to ten milliliters of saline.

The device 10 may be made of any commercially polymeric material. One preferred configuration of the device 10 is made of an elastomer plastic selected from the group consisting of polyester, polypropylene, polyurethanes, polyacryls, polymethacryls, cellulosic polymers, styrene-acryl copolymers, polystyrene-polyacryl mixtures, polysiloxanes, urethane-acryl copolymers, siloxane-urethane copolymers, polyurethane-polymethacryl mixtures, silicone 20-acryl copolymers, vinyl acetate polymers, and mixtures thereof.

The device may be sterile or sanitized. One preferred configuration is that the device is sterile.

The volumetric capacity of the collection bag 52 may be any size. One preferred configuration is that the collection bag 52 having a capacity selected from the group consisting of approximately one half liter, approximately two liters, and approximately four liters.

One preferred embodiment of a method of using a urethral catheter device 10, the method comprising the steps of aligning, forcing, holding, injecting, inserting, lubricating, positioning, releasing, removing, sliding, slipping, turning, and twisting. The obtaining step comprises obtaining the device 10 comprising: a catheter probe 12 comprising: an elongated shaft 14 including: an interior side wall; an exterior side wall; a middle section; a proximate end for insertion into a bladder 56 of a patient; a distal end for pending outside the bladder 56 of the patient; and an internal wall disposed between the interior side wall and the exterior side wall, wherein the internal wall of the shaft 14 defining a lip disposed at the exterior side wall of the shaft 14, the lip defining a saline outlet 34 disposed in the proximate end of the shaft 14; a drainage lumen 16 defined by the interior side wall of the shaft 14, the drainage lumen 16 providing fluid communication between the proximate end of the shaft 14 and the distal end of the shaft 14; a drainage inlet 18 comprising a drainage opening defined by the drainage lumen 16 at the proximate end of the shaft 14, the drainage inlet 18 for receiving urine from the bladder 56; a tapered cone 20 attached to the proximate end of the shaft 14, the cone 20 having a pointed head 24 and a drainage outlet 22, the drainage outlet 22 of the cone 20 in fluid communication with the drainage inlet 18, the drainage outlet 22 for discharging urine; a collar 26 attached to the distal end of the shaft 14, the collar 26 having an annular interior wall, the interior wall of the collar 26 having two ridges defining an annular channel disposed around the interior wall of the collar 26; an elongated protuberance 28 attached to the middle section of the shaft 14, the protuberance 28 including: a distal end, the distal end of the protuberance 28 is attached to the middle section of the shaft 14; a proximate end; an inner side wall, the inner side wall of the protuberance 28 connected to the internal wall of the shaft 14; and an outer side wall; a saline inlet 30 defined by the inner side wall of the protuberance 28, the saline inlet 30 disposed at the proximate end of the protuberance 28, the saline inlet 30 for receiving saline; a saline lumen 32 defined by the internal wall of the shaft 14 and the inner side wall of the protuberance 28, the saline lumen 32 in fluid communications with the saline inlet 30 of the protuberance 28 and the saline outlet 34 of the shaft 14; a sheath 36 circumferentially attached around the proximate end of the shaft 14, the sheath 36 defining a void space between the sheath 36 and the proximate end of the shaft 14, the void space in fluid communications with saline outlet 34 disposed of the shaft 14, wherein when the void space is empty then the sheath 36 is collapsed around the proximate end of the shaft 14, when the void space is filled with saline then the sheath 36 expands into a donut shaped balloon, the drainage inlet 18 disposed outside of the balloon; and a fluid lock 38 pivotally attached to the proximate end of the protuberance 28, the fluid lock 38 is in fluid communications with the saline inlet 30, when the fluid lock 38 is turned in a given direction then the fluid lock 38 is placed in an open position so that the saline inlet 30 is in fluid communications with the surrounding environment of the device 10, when the fluid lock 38 is rotated in an opposite direction relative to the given direction then the fluid lock 38 is in a closed position wherein the saline inlet 30 is not in fluid communications with the surrounding environment of the device 10; at least one receiving unit 40 attachable to the probe 12, each receiving unit 40 of the at least one receiving unit 40 comprising: a sterile membrane 42; a sleeve 44 attached to the membrane 42, the sleeve 44 having rim 46 attached to the membrane 42; an annular outside wall, the annular outside wall having an annular ring 48 attached around the outside wall, the annular outside wall is proportioned to slidably insert within the collar 26 of the distal end of the shaft 14, the ring 48 of the outside wall of the sleeve 44 is shaped to slidably lock within the annular channel disposed around the interior wall of the collar 26 of the distal end of the shaft 14, wherein when the sleeve 44 is inserted within the collar 26 of the distal end of the shaft 14 then the membrane 42 is punctured with the pointed head 24 of the cone 20 of the shaft 14; and an annular inside wall, the annular inside wall defining a urine collection inlet 50; and a collection bag 52 attached to the sleeve 44, the collection bag 52 in fluid communications with the urine collection inlet 50 of the sleeve 44; and a cap 54 attached to the outside wall of the sleeve 44 of each receiving unit 40 of the at least one receiving unit 40, wherein the sterile membrane 42 of each receiving unit 40 of the at least one receiving unit 40 is disposed between the cap 54 and the rim 46 of the sleeve 44. The holding step comprises holding with a hand onto a penis of the patient. The lubricating step comprises lubricating the proximate end of the shaft 14 of the probe 12 with a gel. The aligning step comprises aligning the lubricated proximate end of the shaft 14 of the probe 12 with the external urethral orifice of the held penis of the patient. The inserting step comprises inserting the lubricated proximate end of the shaft 14 of the probe 12 into the external urethral orifice of the held penis of the patient. The slipping step comprises slipping the lubricated proximate end of the shaft 14 of the probe 12 through the urethra of the held penis of the patient. The forcing step comprises forcing the lubricated proximate end of the shaft 14 of the probe 12 through the prostate gland of the patient. The positioning step comprises positioning the lubricated proximate end of the shaft 14 of the probe 12 in the bladder 56 of the patient. The releasing step comprises releasing with the hand from the penis of the patient. The turning step comprises turning the fluid lock 38 in the given direction so that the fluid lock 38 is placed in the open position. The injecting step comprises injecting about five to ten milliliters of saline into the saline inlet 30 when the fluid lock 38 is placed in the open position so that the sheath 36 is allowed to expand into the donut shaped balloon when the lubricated proximate end of the shaft 14 of the probe 12 is positioned in the bladder 56 of the patient. The twisting step comprises twisting the fluid lock 38 in the opposite direction relative to the given direction so that the fluid lock 38 is placed in the closed position, the twisting step performed subsequent to the injecting step. The removing step comprises removing away the cap 54 from the outside wall of the sleeve 44 of the receiving unit 40. The sliding step comprises sliding the sleeve 44 within the collar 26 of the distal end of the shaft 14, so that the ring 48 of the outside wall of the sleeve 44 locks within the annular channel disposed around the interior wall of the collar 26 of the distal end of the shaft 14, wherein puncturing 48 the membrane 42 thereby establishing a fluid communication between the drainage inlet 18 at the proximate end of the shaft 14 with the collection bag 52 of the receiving unit 40. The valve in the distal end of the shaft 14 is opened by connecting drainage bag, or may alternatively be opened manually by pinching the distal end.

Referring now to FIG. 1 which depicts is a perspective view of an preferred embodiment of the urethral catheter device 10 showing the catheter probe 12 attached to the receiving unit 40. The catheter probe 12 is shown having a elongated shaft 14, a drainage inlet 18, a collar 26, an elongated protuberance 28, a saline inlet 30, a sheath 36, and a fluid lock 38. The elongated shaft 14 is shown having an exterior side wall; a middle section; a proximate end for insertion into a bladder 56 of a patient; and a distal end for pending outside the bladder 56 of the patient. The drainage inlet 18 is shown comprising a drainage opening defined by the drainage lumen 16 at the proximate end of the shaft 14, wherein the drainage inlet 18 is for receiving urine from the bladder 56. The collar 26 is shown attached to the distal end of the shaft 14. The elongated protuberance 28 is shown attached to the middle section of the shaft 14, wherein the protuberance 28 is shown having a distal end is attached to the middle section of the shaft 14; a proximate end; and an outer side wall. The saline inlet 30 is shown defined by the inner side wall of the protuberance 28, in which the saline inlet 30 is disposed at the proximate end of the protuberance 28, whereby the saline inlet 30 for receiving saline. The sheath 36 is shown circumferentially attached around the proximate end of the shaft 14, in which the sheath 36 defines a void space between the sheath 36 and the proximate end of the shaft 14, wherein the void space is shown expanded into the donut shaped balloon, in which the drainage inlet 18 is shown disposed outside of the balloon. The fluid lock 38 is shown pivotally attached to the proximate end of the protuberance 28, wherein the fluid lock 38 is in fluid communications with the saline inlet 30. The receiving unit 40 is shown having a sleeve 44 attached to a collection bag 52.

Figure 2:
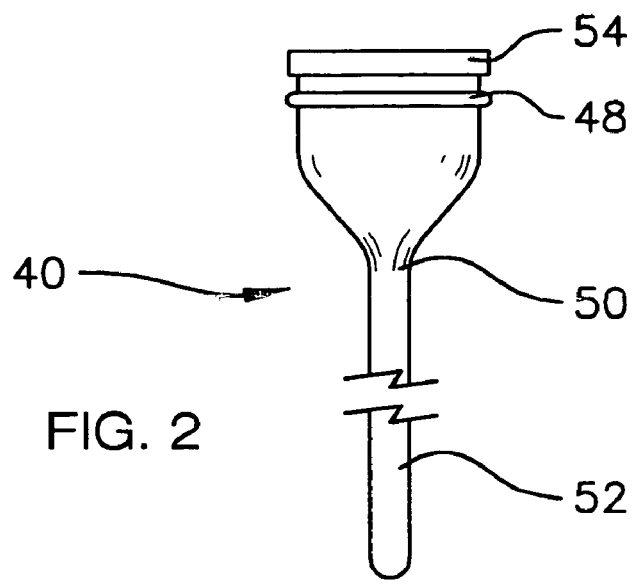
FIG. 2 is a side plan view of a preferred embodiment of the receiving unit of the urethral catheter device of the present invention.

Referring now to FIG. 2 which depicts a side plan view of a preferred embodiment of the receiving unit 40 of the urethral catheter device 10 showing the receiving unit 40 comprises: a sleeve 44 attached to the collection bag 52 in which a cap 54 is shown attached to the sleeve 44. The sleeve 44 is shown having an annular outside wall in which the annular outside wall is shown having an annular ring 48 attached around the outside wall. The annular outside wall is designed to slidably insert within the collar 26 of the distal end of the shaft 14, wherein the ring 48 of the outside wall of the sleeve 44 is shaped to slidably lock within the annular. The collection bag 52 is shown attached to the sleeve 44, in which the collection bag 52 in fluid communications with the urine collection inlet 50 of the sleeve 44.

Figure 3:
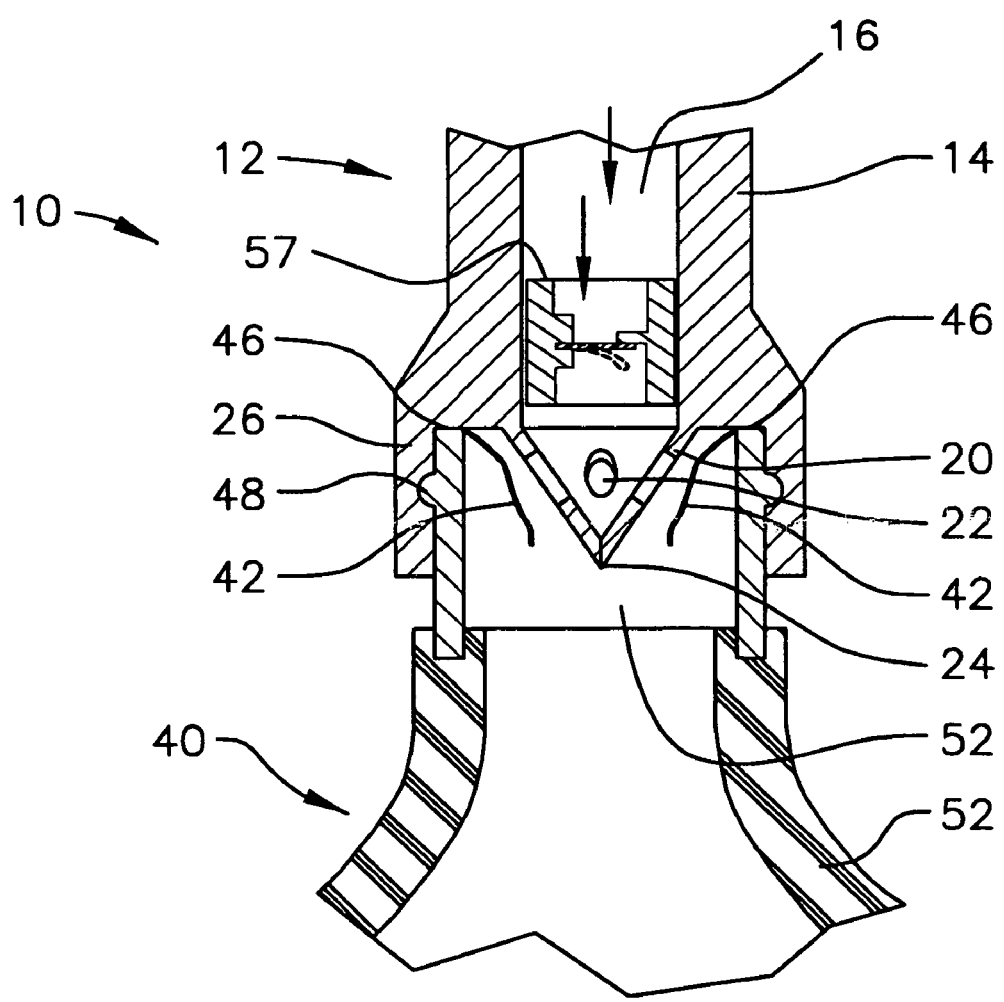
FIG. 3 is a closeup cross sectional side view of a preferred embodiment of the urethral catheter device of the present invention.

Referring now to FIG. 3 which depicts a closeup cross sectional side view of a preferred embodiment of the urethral catheter device 10 showing the catheter probe 12 attached to a receiving unit 40. The catheter probe 12 is shown having an elongated shaft 14, a drainage lumen 16, a tapered cone 20, and a collar 26. The elongated shaft 14 is shown having an interior side wall; an exterior side wall; a middle section; and a distal end comprising a valve 57 for pending outside the bladder of the patient. The drainage lumen 16 is shown defined by the interior side wall of the shaft 14, in which the drainage lumen 16 provides fluid communication between the proximate end of the shaft 14 and the distal end of the shaft 14. The tapered cone 20 is shown attached to the proximate end of the shaft 14, in which the cone 20 is shown having a pointed head 24 and a drainage outlet 22. The collar 26 is shown attached to the distal end of the shaft 14, wherein the collar 26 has an annular interior wall, in which the interior wall of the collar 26 has two ridges defining an annular channel disposed around the interior wall of the collar 26. The receiving unit 40 is shown attached to the catheter probe 12 in which the receiving unit 40 is shown having a sterile membrane 42, a sleeve 44, and a collection bag 52. The sleeve 44 is shown attached to the membrane 42. The sleeve 44 is shown having a rim 46, an annular outside wall, and an annular inside wall. The rim 46 of the sleeve 44 is shown attached to the membrane 42. The annular outside wall is shown having an annular ring 48 attached around the outside wall, in which the annular outside wall is shown to be proportioned to slidably insert within the collar 26 of the distal end of the shaft 14, wherein the ring 48 of the outside wall of the sleeve 44 is shown shaped to slidably lock within the annular channel disposed around the interior wall of the collar 26 of the distal end of the shaft 14. The membrane 42 is shown punctured with the pointed head 24 of the cone 20 of the shaft 14 when the sleeve 44 is inserted within the collar 26 of the distal end of the shaft 14. The annular inside wall is shown defining the urine collection inlet 50. The collection bag 52 is shown attached to the sleeve 44, in which the collection bag 52 in fluid communications with the urine collection inlet 50 of the sleeve 44.

Figures 4, 5:
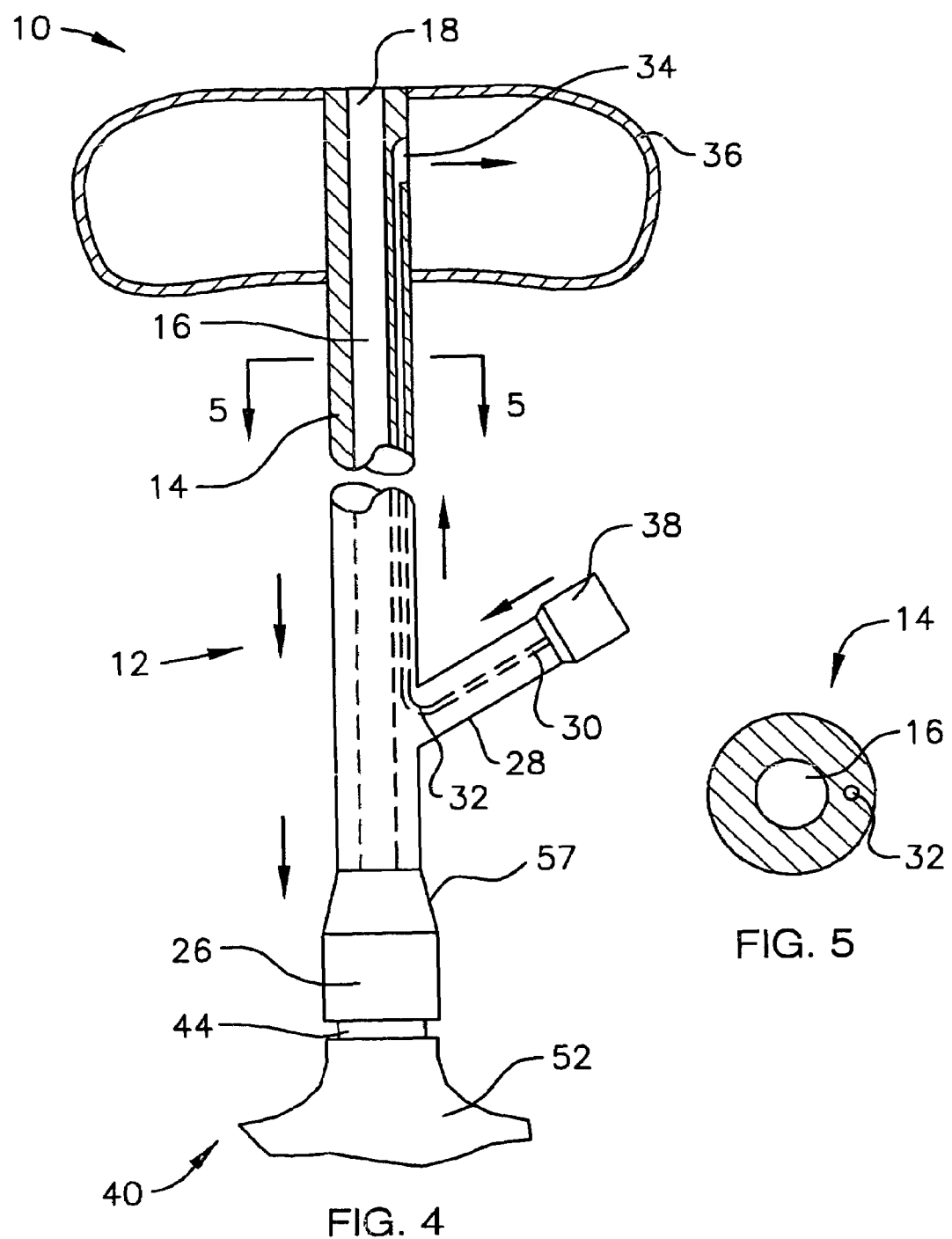
FIG. 4 is a partial cross sectional side view of a preferred embodiment of the urethral catheter device of the present invention.
FIG. 5 is a cross sectional front view of a preferred embodiment of the urethral catheter device of the present invention.

Referring now to FIG. 4, which depicts a partial cross sectional side view of a preferred embodiment of the urethral catheter device 10 showing the catheter probe 12 attached to a receiving unit 40. The catheter probe 12 is shown comprising: an elongated shaft 14, a drainage lumen 16, a drainage inlet 18, a collar 26, an elongated protuberance 28, a saline inlet 30, a saline lumen 32, a sheath 36, and a fluid lock 38. The elongated shaft 14 is shown to include: an interior side wall; an exterior side wall; a middle section; a proximate end for insertion into a bladder 56 of a patient; a distal end having a valve 57 for pending outside the bladder 56 of the patient; and an internal wall disposed between the interior side wall and the exterior side wall, wherein the internal wall of the shaft 14 is shown defining a lip disposed at the exterior side wall of the shaft 14, the lip is shown defining a saline outlet 34 disposed in the proximate end of the shaft 14. The drainage lumen 16 is shown defined by the interior side wall of the shaft 14. The drainage inlet 18 is shown comprising a drainage opening defined by the drainage lumen 16 at the proximate end of the shaft 14, wherein the drainage inlet 18 is for receiving urine from the bladder 56. The collar 26 is shown attached to the distal end of the shaft 14. The elongated protuberance 28 is shown attached to the middle section of the shaft 14, wherein the protuberance 28 is shown to include: a distal end, the distal end of the protuberance 28 is shown attached to the middle section of the shaft 14; a proximate end; an inner side wall, the inner side wall of the protuberance 28 connected to the internal wall of the shaft 14; and an outer side wall. The saline inlet 30 is shown defined by the inner side wall of the protuberance 28, in which the saline inlet 30 is disposed at the proximate end of the protuberance 28, whereby the saline inlet 30 for receiving saline. The saline lumen 32 is shown defined by the internal wall of the shaft 14 and the inner side wall of the protuberance 28, wherein the saline lumen 32 is in fluid communications with the saline inlet 30 of the protuberance 28 and the saline outlet 34 of the shaft 14. The sheath 36 is shown circumferentially attached around the proximate end of the shaft 14, in which the sheath 36 is shown defining a void space between the sheath 36 and the proximate end of the shaft 14. The void space is shown in fluid communications with saline outlet 34 disposed of the shaft 14. The void space is shown expanded into a donut shaped balloon, wherein the drainage inlet 18 is shown disposed outside of the balloon. The fluid lock 38 is shown pivotally attached to the proximate end of the protuberance 28, wherein the fluid lock 38 is in fluid communications with the saline inlet 30. The receiving unit 40 is shown comprising a sleeve 44, and a collection bag 52.

Referring now to FIG. 5 which depicts a cross sectional front view of the elongated shaft 14 showing an interior side wall; an exterior side wall; and an internal wall disposed between the interior side wall and the exterior side wall. The drainage lumen 16 is shown defined by the interior side wall of the shaft 14. The saline lumen 32 is shown defined by the internal wall of the shaft 14 and the inner side wall of the protuberance 28 (not shown).

As to the manner of usage and operation of the present invention, the same should be apparent from the above description. Accordingly, no further discussion relating to the manner of usage and operation will be provided.

While a preferred embodiment of the urethral catheter device has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Throughout this specification, unless the context requires otherwise, the word "comprise" or variations such as "comprises" or "comprising" or the term "includes" or variations, thereof, or the term "having" or variations, thereof will be understood to imply the inclusion of a stated element or integer or group of elements or integers but not the exclusion of any other element or integer or group of elements or integers. In this regard, in construing the claim scope, an embodiment where one or more features is added to any of the claims is to be regarded as within the scope of the invention given that the essential features of the invention as claimed are included in such an embodiment.

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combinations of any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A urethral catheter device comprising:
    a catheter probe comprising:
        an elongated shaft including:
            an interior side wall;
            an exterior side wall;
            a middle section;
            a proximate end for insertion into a bladder of a patient;
            a distal end comprising a valve for pending outside the bladder of the patient; and
            an internal wall disposed between said interior side wall and said exterior side wall, wherein said internal wall of said shaft defining a lip disposed at the exterior side wall of said shaft, said lip defining a saline outlet disposed in said proximate end of said shaft;
        a drainage lumen defined by said interior side wall of said shaft, said drainage lumen providing fluid communication between said proximate end of said shaft and said distal end of said shaft;
        a drainage inlet comprising a drainage opening defined by said drainage lumen at said proximate end of said shaft, said drainage inlet for receiving urine from the bladder;
        a tapered cone attached to the distal end of said shaft, said cone having a pointed head and a side port drainage outlet, said drainage outlet of said cone in fluid communication with said drainage inlet, said drainage outlet for discharging urine;
        a collar attached to the distal end of said shaft, said collar having an annular interior wall, said interior wall of said collar having two ridges defining an annular channel disposed around said interior wall of said collar;
        an elongated protuberance attached to said middle section of said shaft, said protuberance including:
            a distal end, the distal end of said protuberance is attached to said middle section of said shaft;
            a proximate end;
            an inner side wall, said inner side wall of said protuberance connected to said internal wall of said shaft; and
            an outer side wall;
        a saline inlet defined by said inner side wall of said protuberance, said saline inlet disposed at said proximate end of said protuberance, said saline inlet for receiving saline;
        a saline lumen defined by said internal wall of said shaft and said inner side wall of said protuberance, said saline lumen in fluid communications with said saline inlet of said protuberance and said saline outlet of said shaft;
        a sheath circumferentially attached around said proximate end of said shaft, said sheath defining a void space between said sheath and said proximate end of said shaft, said void space in fluid communications with saline outlet disposed of said shaft, wherein when said void space is empty then said sheath is collapsed around said proximate end of said shaft, when said void space is filled with saline then said sheath expands into a donut shaped balloon, said drainage inlet disposed outside of said balloon; and a fluid lock pivotally attached to said proximate end of said protuberance, said fluid lock is in fluid communications with said saline inlet, when said fluid lock is turned in a given direction then said fluid lock is placed in an open position so that said saline inlet is in fluid communications with the surrounding environment of the device, when said fluid lock is rotated in an opposite direction relative to said given direction then said fluid lock is in a closed position wherein said saline inlet is not in fluid communications with the surrounding environment of the device; and at least one receiving unit attachable to said probe, each receiving unit of said at least one receiving unit comprising:

a sterile membrane;

a sleeve attached to said membrane, said sleeve having rim attached to said membrane;

an annular outside wall, said annular outside wall having an annular ring attached around said outside wall, said annular outside wall is proportioned to slidably insert within said collar of said distal end of said shaft, said ring of said outside wall of said sleeve is shaped to slidably lock within said annular channel disposed around said interior wall of said collar of said distal end of said shaft, wherein when said sleeve is inserted within said collar of said distal end of said shaft then said membrane is punctured with said pointed head of said cone of said shaft; and an annular inside wall, said annular inside wall defining a urine collection inlet; and a collection bag attached to the sleeve, said collection bag in fluid communications with said urine collection inlet of said sleeve.

2. The device of claim 1 further comprising at least one cap, each cap of said at least one cap is attached to said outside wall of said sleeve of each receiving unit of said at least one receiving unit, wherein said sterile membrane of each receiving unit of said at least one receiving unit is disposed between said cap and said rim of said sleeve.

3. The device of claim 1 wherein said void space between said sheath and said proximate end of said shaft having a volumetric capacity of at least five milliliters of saline.

4. The device of claim 1 wherein said void space between said sheath and said proximate end of said shaft having a volumetric capacity of up to ten milliliters of saline.

5. The device of claim 1 wherein said device is made of an elastomer plastic selected from the group consisting of polyester, polypropylene, polyurethanes, polyacryls, polymethacryls, cellulosic polymers, styrene-acryl copolymers, polystyrene-polyacryl mixtures, polysiloxanes, urethane-acryl copolymers, siloxane-urethane copolymers, polyurethane-polymethacryl mixtures, silicone-acryl copolymers, vinyl acetate polymers, and mixtures thereof.

6. The device of claim 1 wherein said device is sterile.

7. The device of claim 1 wherein said collection bag having a capacity of approximately one half liter.

8. The device of claim 1 wherein said collection bag having a capacity of approximately one liter.

9. The device of claim 1 wherein said collection bag having a capacity of approximately two liters.

10. The device of claim 1 wherein said collection bag having a capacity of approximately four liters.

11. A urethral catheter device consisting essentially of:

a catheter probe comprising:

an elongated shaft including:

an interior side wall;

an exterior side wall;

a middle section;

a proximate end for insertion into a bladder of a patient;

a distal end comprising a valve for pending outside the bladder of the patient; and an internal wall disposed between said interior side wall and said exterior side wall, wherein said internal wall of said shaft defining a lip disposed at the exterior side wall of said shaft, said lip defining a saline outlet disposed in said proximate end of said shaft;

a drainage lumen defined by said interior side wall of said shaft, said drainage lumen providing fluid communication between said proximate end of said shaft and said distal end of said shaft;

a drainage inlet comprising a drainage opening defined by said drainage lumen at said proximate end of said shaft, said drainage inlet for receiving urine from the bladder;

a tapered cone attached to the distal end of said shaft, said cone having a pointed head and a side port drainage outlet, said drainage outlet of said cone in fluid communication with said drainage inlet, said drainage outlet for discharging urine;

a collar attached to the distal end of said shaft, said collar having an annular interior wall, said interior wall of said collar having two ridges defining an annular channel disposed around said interior wall of said collar;

an elongated protuberance attached to said middle section of said shaft, said protuberance including:

a distal end, comprising a valve, said distal end attached to said middle section of said shaft;

a proximate end;

an inner side wall, said inner side wall of said protuberance connected to said internal wall of said shaft; and an outer side wall;

a saline inlet defined by said inner side wall of said protuberance, said saline inlet disposed at said proximate end of said protuberance, said saline inlet for receiving saline;

a saline lumen defined by said internal wall of said shaft and said inner side wall of said protuberance, said saline lumen in fluid communications with said saline inlet of said protuberance and said saline outlet of said shaft;

a sheath circumferentially attached around said proximate end of said shaft, said sheath defining a void space between said sheath and said proximate end of said shaft, said void space in fluid communications with saline outlet disposed of said shaft, wherein when said void space is empty then said sheath is collapsed around said proximate end of said shaft, when said void space is filled with saline then said sheath expands into a donut shaped balloon, said drainage inlet disposed outside of said balloon; and a fluid lock pivotally attached to said proximate end of said protuberance, said fluid lock is in fluid communications with said saline inlet, when said fluid lock is turned in a given direction then said fluid lock is placed in an open position so that said saline inlet is in fluid communications with the surrounding environment of the device, when said fluid lock is rotated in an opposite direction relative to said given direction then said fluid lock is in a closed position wherein said saline inlet is not in fluid communications with the surrounding environment of the device;

at least one receiving unit attachable to said probe, each receiving unit of said at least one receiving unit comprising:
a sterile membrane;
a sleeve attached to said membrane, said sleeve having rim attached to said membrane;
an annular outside wall, said annular outside wall having an annular ring attached around said outside wall, said annular outside wall is proportioned to slidably insert within said collar of said distal end of said shaft, said ring of said outside wall of said sleeve is shaped to slidably lock within said annular channel disposed around said interior wall of said collar of said distal end of said shaft, wherein when said sleeve is inserted within said collar of said distal end of said shaft then said membrane is punctured with said pointed head of said cone of said shaft; and
an annular inside wall, said annular inside wall defining a urine collection inlet; and
a collection bag attached to the sleeve, said collection bag in fluid communications with said urine collection inlet of said sleeve; and at least one cap, each cap of said at least one cap is attached to said outside wall of said sleeve of each receiving unit of said at least one receiving unit, wherein said sterile membrane of each receiving unit of said at least one receiving unit is disposed between said cap and said rim of said sleeve.

12. The device of claim 11 wherein said void space between said sheath and said proximate end of said shaft having a volumetric capacity of at least five milliliters of saline.

13. The device of claim 1 wherein said void space between said sheath and said proximate end of said shaft having a volumetric capacity of up to ten milliliters of saline.

14. The device of claim 11 wherein said device is made of an elastomer plastic selected from the group consisting of polyester, polypropylene, polyurethanes, polyacryls, polymethacryls, cellulosic polymers, styrene-acryl copolymers, polystyrene-polyacryl mixtures, polysiloxanes, urethane-acryl copolymers, siloxane-urethane copolymers, polyurethane-polymethacryl mixtures, silicone-acryl copolymers, vinyl acetate polymers, and mixtures thereof.

15. The device of claim 11 wherein said device is sterile.

16. The device of claim 11 wherein said collection bag having a capacity of approximately one half liter.

17. The device of claim 11 wherein said collection bag having a capacity of approximately one liter.

18. The device of claim 11 wherein said collection bag having a capacity of approximately two liters.

19. The device of claim 1I wherein said collection bag having a capacity of approximately four liters.

20. A method of using a urethral catheter device, said method comprising the steps of:
obtaining the device comprising:
a catheter probe comprising:
an elongated shaft including:
an interior side wall;
an exterior side wall;
a middle section;
a proximate end for insertion into a bladder of a patient;
a distal end having a valve therein; and
an internal wall disposed between the interior side wall and the exterior side wall, wherein the internal wall of the shaft defining a lip disposed at the exterior side wall of the shaft, the lip defining a saline outlet disposed in the proximate end of the shaft;
a drainage lumen defined by the interior side wall of the shaft, the drainage lumen providing fluid communication between the proximate end of the shaft and the distal end of the shaft;
a drainage inlet comprising a drainage opening defined by the drainage lumen at the proximate end of the shaft, the drainage inlet for receiving urine from the bladder;
a tapered cone attached to the distal end of the shaft, the cone having a pointed head and a side port drainage outlet, the drainage outlet of the cone in fluid communication with the drainage inlet, the drainage outlet for discharging urine;
a collar attached to the distal end of the shaft, the collar having an annular interior wall, the interior wall of the collar having two ridges defining an annular channel disposed around the interior wall of the collar;
an elongated protuberance attached to the middle section of the shaft, the protuberance including:
a distal end, the distal end of the protuberance having a valve therein and attached to the middle section of the shaft;
a proximate end;
an inner side wall, the inner side wall of the protuberance connected to the internal wall of the shaft; and
an outer side wall;
a saline inlet defined by the inner side wall of the protuberance, the saline inlet disposed at the proximate end of the protuberance, the saline inlet for receiving saline;
a saline lumen defined by the internal wall of the shaft and the inner side wall of the protuberance, the saline lumen in fluid communications with the saline inlet of the protuberance and the saline outlet of the shaft;
a sheath circumferentially attached around the proximate end of the shaft, the sheath defining a void space between the sheath and the proximate end of the shaft, the void space in fluid communications with saline outlet disposed of the shaft, wherein when the void space is empty then the sheath is collapsed around the proximate end of the shaft, when the void space is filled with saline then the sheath expands into a donut shaped balloon, the drainage inlet disposed outside of the balloon; and
a fluid lock pivotally attached to the proximate end of the protuberance, the fluid lock is in fluid communications with the saline inlet, when the fluid lock is turned in a given direction then the fluid lock is placed in an open position so that the saline inlet is in fluid communications with the surrounding environment of the device, when the fluid lock is rotated in an opposite direction relative to the given direction then the fluid lock is in a closed position wherein the saline inlet is not in fluid communications with the surrounding environment of the device;
at least one receiving unit attachable to the probe, each receiving unit of the at least one receiving unit comprising:
a sterile membrane;
a sleeve attached to the membrane, the sleeve having rim attached to the membrane;
an annular outside wall, the annular outside wall having an annular ring attached around the outside wall, the annular outside wall is proportioned to slidably insert within the collar of the distal end of the shaft, the ring of the outside wall of the sleeve is shaped to slidably lock within the annular channel disposed around the interior wall of the collar of the distal end of the shaft, wherein when the sleeve is inserted within the collar of the distal end of the shaft then the membrane is punctured with the pointed head of the cone of the shaft; and
an annular inside wall, the annular inside wall defining a urine collection inlet; and
a collection bag attached to the sleeve, the collection bag in fluid communications with the urine collection inlet of the sleeve; and
a cap attached to the outside wall of the sleeve of each receiving unit of the at least one receiving unit, wherein the sterile membrane of each receiving unit of the at least one receiving unit is disposed between the cap and the rim of the sleeve;
holding with a hand onto a penis of the patient;
lubricating the proximate end of the shaft of the probe with a gel;
aligning the lubricated proximate end of the shaft of the probe with the external urethral orifice of the held penis of the patient;
inserting the lubricated proximate end of the shaft of the probe into the external urethral orifice of the held penis of the patient;
slipping the lubricated proximate end of the shaft of the probe through the urethra of the held penis of the patient;
forcing the lubricated proximate end of the shaft of the probe through the prostate gland of the patient;
positioning the lubricated proximate end of the shaft of the probe in the bladder of the patient;
releasing with the hand from the penis of the patient;
turning the fluid lock in the given direction so that the fluid lock is placed in the open position;
injecting about five to ten milliliters of saline into the saline inlet when the fluid lock is placed in the open position so that the sheath is allowed to expand into the donut shaped balloon when the
lubricated proximate end of the shaft of the probe is positioned in the bladder of the patient;
twisting the fluid lock in the opposite direction relative to the given direction so that the fluid lock is placed in the closed position, said twisting step performed subsequent to said injecting step;
removing away the cap from the outside wall of the sleeve of the receiving unit; and
sliding the sleeve within the collar of the distal end of the shaft, so that the ring of the outside wall of the sleeve locks within the annular channel disposed around the interior wall of the collar of the distal end of the shaft, wherein said pointed head of said tapered cone punctures the membrane, thereby establishing a fluid communications between the drainage inlet at the proximate end of the shaft with the collection bag of the receiving unit.

* * * * *